United States Patent [19]

Bassim et al.

[11] Patent Number: 4,609,994

[45] Date of Patent: Sep. 2, 1986

[54] APPARATUS FOR CONTINUOUS LONG-TERM MONITORING OF ACOUSTIC EMISSION

[75] Inventors: M. Nabil Bassim; Kris Tangri, both of Manitoba, Canada

[73] Assignee: The University of Manitoba, Winnipeg, Canada

[21] Appl. No.: 570,866

[22] Filed: Jan. 16, 1984

[51] Int. Cl.[4] .................. G01S 5/18; G06F 15/46
[52] U.S. Cl. ..................... 364/551; 73/577; 73/587
[58] Field of Search .............. 364/551, 554; 73/570, 73/577, 587

[56] References Cited

U.S. PATENT DOCUMENTS

| | | | |
|---|---|---|---|
| 3,545,262 | 12/1970 | Steele et al. | 73/37 |
| 3,774,443 | 11/1973 | Green et al. | 73/577 |
| 3,855,847 | 12/1974 | Leschek | 73/587 |
| 3,924,456 | 12/1975 | Vahaviolos | 73/770 |
| 3,946,600 | 3/1976 | Bettig et al. | 73/587 |
| 3,985,024 | 10/1976 | Horak | 73/587 |
| 4,006,625 | 2/1977 | Davis | 73/587 |
| 4,009,463 | 2/1977 | Vercellotti et al. | 73/587 X |
| 4,036,057 | 7/1977 | Morais | 73/587 |
| 4,128,011 | 12/1978 | Savage | 73/579 |
| 4,184,205 | 1/1980 | Morrow | 73/577 |
| 4,317,368 | 3/1982 | McElroy | 73/587 |
| 4,380,172 | 4/1983 | Imam et al. | 73/659 |
| 4,402,054 | 8/1983 | Osborne et al. | 364/551 X |
| 4,504,905 | 3/1985 | Burrage | 364/551 X |

OTHER PUBLICATIONS

Bassim et al., "Leak Detection in Gas Pipelines with Acoustic Emission", *Proceedings of the International Conference on Pipeline Inspection*, Jun. 13-16, 1983.
"On-Line Nondestructive Testing with Acoustic Emission" Physical Acoustic Corporation, 1981.
"Microcomputer-Based General Purpose Acoustic Emission System", Acoustic Emission Technology Corporation, 1979.
"3000 Series AE Analyzer/Locator," Physical Acoustic Corporation, 1981.
"Acoustic Emission Inspection, a Pipeline Integrity Analysis Tool," D. L. Parry *Proceedings of the Fall Conference of the Society for Nondestructive Testing*, Oct. 1981, pp. 253-272.

*Primary Examiner*—Felix D. Gruber
*Assistant Examiner*—H. R. Herndon
*Attorney, Agent, or Firm*—Woodcock Washburn Kurtz Mackiewicz & Norris

[57] ABSTRACT

Provided is apparatus suitable for continuous long-term monitoring of acoustic emissions, particularly from large structures such as pipelines. The apparatus comprises a plurality of detector-analyzer units coupled to a central control unit via a communications link. Each detector-analyzer unit comprises an acoustic detector, signal processing means, and a microprocessor. Preferably, the signal processing means comprises at least one signal conditioner, and at least one measuring circuit which provides digital output signals representing a set of emission parameters. The microprocessor preferably periodically receives and compares the digital output signal representing each of the emission parameters with the base values thereof, and provides a warning signal if a problem situation is perceived as a result of such comparison.

33 Claims, 2 Drawing Figures

APPARATUS FOR CONTINUOUS LONG-TERM MONITORING OF ACOUSTIC EMISSION

FIELD OF THE INVENTION

This invention relates to apparatus suitable for continuous monitoring of acoustic emission, and more particularly, to apparatus suitable for continuous, on-line, long-term monitoring of acoustic emission from large structures, such as pipelines, to detect incipient failure thereof.

BACKGROUND OF THE INVENTION

Various methods of non-destructive testing and/or monitoring of structures are known. One such method is acoustic emission testing, which detects acoustic emissions (i.e. stress waves) generated in a material when discontinuity growth occurs in same. Discontinuity growth results from fatigue, plastic deformation, cracking, brittle fracture, corrosion pitting and the like. The acoustic emissions or stress waves which are of interest for non-destructive testing purposes take the form of low amplitude pulses, in the 0.1 to 2 MHz frequency range. Acoustic emission testing is a useful means of detecting impending or incipient failure of a structure, since such testing can detect discontinuity growth before it is visible. Acoustic emission equipment can also detect the existence of leaks, in the case of structures containing gases or fluids.

Conventional acoustic emission testing equipment generally consists of one or more piezoelectric transducers which are attached to the surface of the structure being tested and which are coupled to a data analysis unit of one or more channels. The output of each transducer is typically amplified, conditioned (such as by filtering) and then analyzed by the data analysis unit. Typical parameters generated by the analysis unit include emission counts, count rate, amplitude and energy. These parameters are generally displayed as a function of time on either a hard copy recorder or a video display terminal, and are reviewed and interpreted by a trained operator, to determine the existence and nature of any discontinuities or leaks.

Most acoustic emission testing systems require that a source of stress, such as hydrostatic pressure, be applied thereto, in order to determine the existence of discontinuity growth. This type of equipment, which is geared to periodic and proof testing of structures, is limited, since it cannot provide any monitoring of the structure during operating conditions, i.e. it cannot provide on-line monitoring capability.

Some acoustic emission testing equipment is said to be capable of providing limited on-line monitoring to detect certain discontinuities, for some applications. For instance, U.S. Pat. No. 4,380,172, which issued to Imam et al on Apr. 19, 1983, discloses a method for detecting incipient cracks in the rotor of a fluid powered turbine; and U.S. Pat. No. 4,317,368, which issued to McElroy on Mar. 2, 1982, discloses an apparatus which detects acoustic emissions produced in a fibreglass boom by breakage of glass fibres.

However, these and other known acoustic emission testing or monitoring systems are not well adapted to economically analyze the output of more than only a few acoustic emission detectors, since multichannel analyzers of more than only a few channels are expensive. Most of these systems are also very expensive to operate continuously for more than a few hours of time, since generally a highly trained scientist or technician must be continuously present to interpret the output of the analyzer and make decisions based thereon. In particular, it has been found that conventional acoustic emission monitoring equipment is incapable of economically monitoring a large structure such as a pipeline extending for several kilometers under operating conditions on a continuous, long-term basis (i.e. 24 hours a day for days or weeks), in view of the large number of detectors required (several hundred for some cases), and in view of the overwhelming amount of data which is generated therefrom and which must be analyzed and interpreted, in order to obtain meaningful results.

SUMMARY OF THE INVENTION

It has been found that economical, long-term, on-line surveillance of the integrity of large structures can be achieved by means of an acoustic emission monitoring system having a plurality of detector-analyzer units coupled to a central control unit.

Accordingly, the present invention provides apparatus suitable for continuous long-term monitoring of acoustic emissions, comprising a plurality of detector-analyzer units, each in a discrete pre-selected location, and a central control unit remote from and coupled to each of the detector-analyzer units. Each detector-analyzer unit includes an acoustic detector, at least one signal conditioner (which may include one or more amplifiers, filters, and comparators) at least one measuring circuit, and a microprocessor. The acoustic detector detects acoustic emission and provides an output signal representative of the acoustic emission. The signal conditioner is coupled to the detector and receives the output signal therefrom. The signal conditioner provides at least one derivative signal having characteristics correlatable with pre-selected characteristics of the output signal of the detector. (For example, the derivative signal may be frequency selective.) The measuring circuit is coupled to the signal conditioner and receives each derivative signal. The measuring circuit provides for each derivative signal a digital output signal representing one of a set of emission parameters correlatable with said pre-selected characteristics of the output signal of the detector. The microprocessor is coupled to each measuring circuit. It stores a set of base values and also receives and stores the digital output signals representing the set of emission parameters. The microprocessor periodically compares members of the set of base values with corresponding members of the set of emission parameters to determine the existence of a problem situation, and provides a warning signal if any such problem situation is perceived. Suitable communication means are coupled to the microprocessor and remotely to the central control unit for transmission of the warning signal and optionally other data to the central control unit. The central control unit receives any warning signals transmitted by the communication means, and may act as a coordination centre for coordinating and directing a suitable response.

The microprocessor of each detector-analyzer unit preferably includes means for characterizing particular problem situations, and means for controlling the operation of the measuring circuits and signal conditioners. The microprocessor also preferably includes means for providing a message at the time the warning signal is generated, such message including a signal identifying the unit generating the warning signal, a signal representing the set of emission parameters which triggered the warning, and a signal representing the characterization of the problem situation.

The measuring circuit of each detector-analyzer may comprise a total count counter circuit, a count rate counter circuit, and a r.m.s. volt meter circuit. The microprocessor may include a threshold adjustment means, which characterizes incoming data signals as either acoustic emission signals or background noise, based upon whether such signals exceed the current value of a threshold based upon a sampling of previously received data signals. The central control unit preferably includes means for programming and re-programming each detector-analyzer unit with its master program and its set of base values.

The present invention is also directed to a detector-analyzer unit as described above for use with a remote central control unit, the combination thereof being suitable for continuous monitoring of acoustic emission.

According to another aspect of the invention, there is provided a detector-analyzer unit comprising an acoustic detector, signal processing means coupled thereto which provides a digitized output signal, and a microprocessor. The microprocessor includes means for periodically determining a current value of each of a set of emission parameters, means for storing base values for each parameter, means for periodically comparing each current value of the parameter with its base value thereof, and means for providing a warning signal. The invention is also directed to apparatus comprising a plurality of detectors as just described coupled to a central control unit via a communications link.

The invention will now be described, by way of example only, with reference to the following drawings, in which like numerals refer to like parts, and in which:

FIG. 1 is a block diagram illustrating the monitoring apparatus of the present invention shown in conjunction with a pipeline; and FIG. 2 is a block diagram of the preferred embodiment of a detector-analyzer unit made in accordance with the present invention.

DETAILED DESCRIPTION OF THE PREFERRED EMBODIMENT

Figure 1:
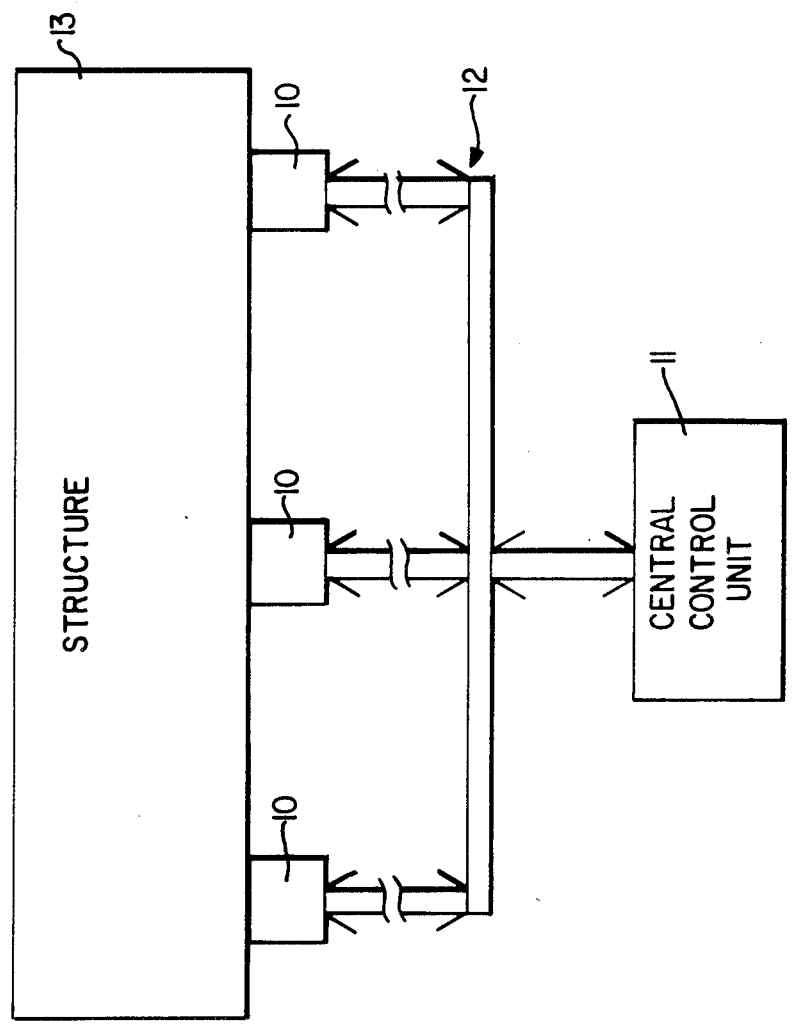

FIG. 1 illustrates the principal components of the monitoring apparatus of the present invention, which comprises a plurality of detector-analyzer units 10 coupled to a central control unit 11, by communications means link 12. Detector-analyzers 10 are shown attached to the surface of pipeline 13, but it is to be understood that the monitoring apparatus of the present invention is also suitable for the surveillance of other structures, particularly large structures, such as nuclear reactors and off-shore drilling platforms, which require continuous surveillance at a large number of discrete locations for long periods of time.

Each detector-analyzer unit 10 is microprocessor controlled and is capable of analyzing the acoustic emissions or stress waves received thereby, by generating a set of emission parameters and by comparing members of this set of parameters with corresponding members of a set of base values for these parameters stored in the memory of the detector-analyzer unit. If this comparison indicates that one or more of the emission parameters exceed the respective base values thereof, a warning signal is generated by the detector-analyzer unit. This warning signal is transmitted to the central control unit 11 by communications means 12. At the same time a further message may be transmitted by the detector-analyzer unit to the control unit which identifies the detector-analyzer unit generating the warning signal and which indicates the current values of the emission parameters (i.e. the values of the parameters at the instant the warning signal was generated).

Each detector-analyzer unit may also be capable of characterizing the type of problem situation, which may be discontinuity growth in the material of the structure, or a leak therefrom of the gas or fluid contained in the structure. The characterization of the problem situation is based upon a known correlation between the response of each of the emission parameters to known problem situations. For example, it is known that cracking tends to increase the count rate parameter, whereas a gas leak tends to increase the r.m.s. voltage parameter. Other problem situations, such as plastic deformation, brittle fracture and fatigue, can be similarly identified. The microprocessor of each detector-analyzer unit can be programmed, based upon the expertise of an experienced interpreter of acoustic emission data, to identify with a reasonable degree of certainty the probable problem situation, depending upon which parameter or combination of parameters have exceeded their base values. This automatic characterization ability of the detector-analyzer unit avoids the need to employ highly trained technicians or scientists to continuously interpret the output of the monitoring apparatus. A signal representing this characterization or identification of a particular problem situation may be transmitted to the central control unit along with the other data discussed above.

The central control unit 11 has the capability of further analyzing, if desired, the information received by each detector-analyzer unit 10. For instance, the central control unit may be programmed to correlate the responses of individual detector-analyzer units, to approximate the location of a discontinuity occurring between adjacent detector-analyzer units.

The apparatus of the present invention therefore provides a two-step method of analysis, with the bulk of the analysis being performed by each detector-analyzer unit. Having most of the analysis performed by each detector-analyzer unit avoids the need for a sophisticated and expensive multi-channel analysis unit. Also avoided is the need to transmit data in analogue form, such data being prone to attenuation over long distances. The difficulties involved in the digitization of raw data in the high kilohertz or megahertz range are also avoided.

The monitoring apparatus of the present invention is particularly suitable for monitoring pipelines of many kilometers long every few hundred meters, such monitoring requiring several hundred individual detectors. No conventional acoustic emission multi-channel analysis system is capable of providing such surveillance in a cost-effective manner, particularly in the case of long-term (days as opposed to minutes), continuous, on-line monitoring.

The central control unit, in addition to including means for receiving messages from the detector-analyzer units, also includes means for programming and re-programming each detector-analyzer unit with its master program and with its set of base values and with its set of measurement variables to be discussed below. The capacity of the central control unit to program the detector-analyzer units is convenient, since the detector-analyzer units will generally be placed in remote, wide-spaced and often inaccessible areas, such as adjacent an underground pipeline. The central control unit 11 is further capable of individually programming each detector-analyzer unit with its own master program and discrete set of base values and measurement variables, if desired. This capability makes the monitoring apparatus of the present invention very flexible and adaptable to various applications.

The central control unit 11 also includes means for testing and monitoring each detector-analyzer unit. More specifically, the central control unit includes means for triggering the self-diagnostic circuit of a given detector-analyzer unit, which is explained below. The central control unit also includes means for receiving and displaying the current set of emission parameters generated by a given detector-analyzer unit at any time.

Figure 2:
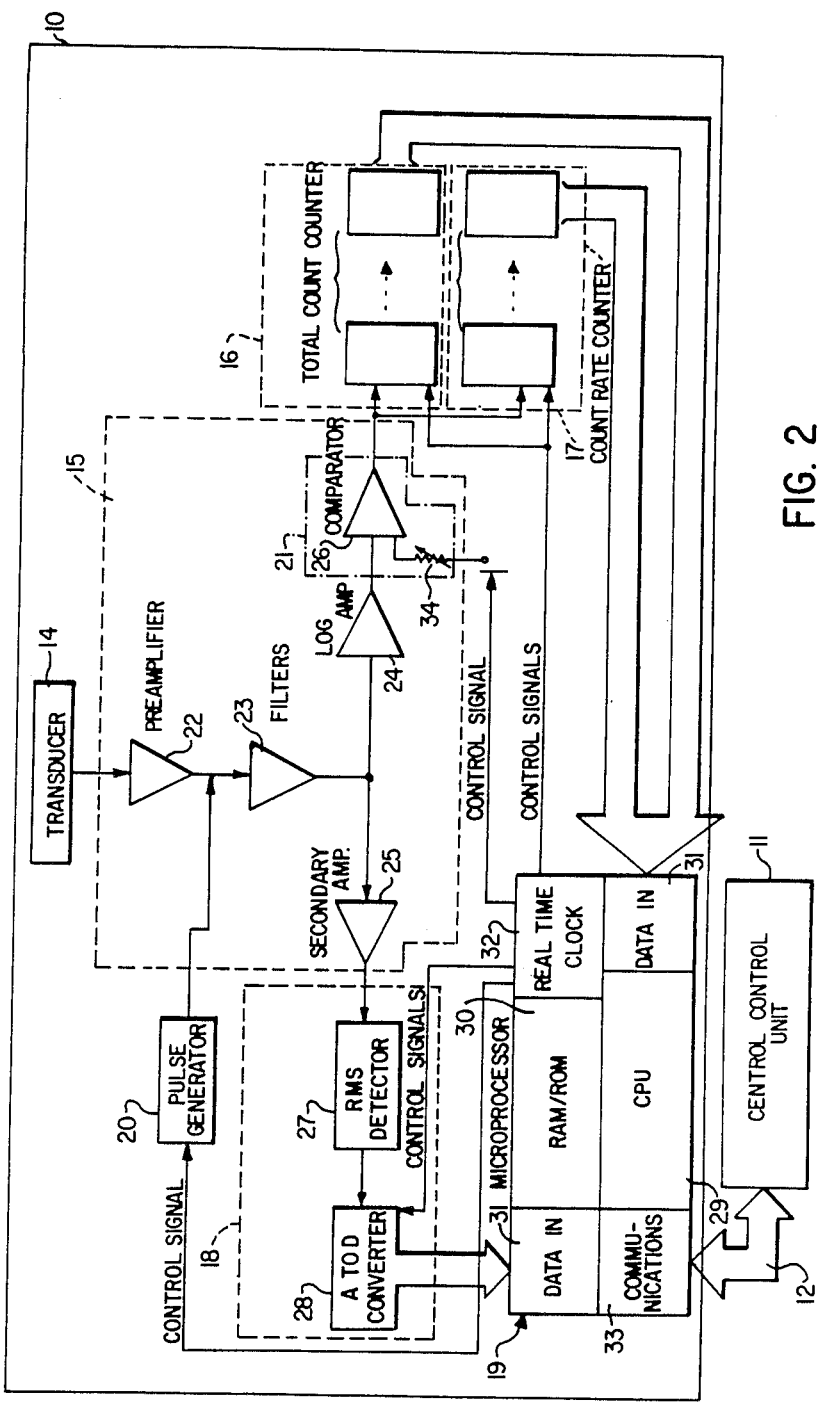

Referring now to FIG. 2, each detector-analyzer unit 10 comprises an acoustic detector 14, a signal conditioner 15, measuring circuits 16, 17 and 18, and microprocessor 19. Each unit 10 is connected to central control unit 11 by means of communication means 12.

Detector 14 detects acoustic emissions generated by a material under stress, and provides an output signal representative of such acoustic emissions, in the sense that its output voltage is proportional to the displacements in the material caused by stress. Detector 14 may be a commercially available acoustic emission piezoelectric transducer or an accelerometer.

Signal conditioner 15 may comprise preamplifier 22, filters 23, logarithmic amplifier 24, secondary amplifier 25, and comparator circuit 21. As such, signal conditioner 15 provides two derivative signals having characteristics correlatable with certain characteristics of the output signal of detector 14. These signals are the output signal of comparator circuit 21 and the output signal of secondary amplifier 25. The latter signal is an amplified and frequency-filtered version of the output of detector 14. The output signal of the comparator is described below.

Preamplifier 22 may be an N-channel Field Effect Transistor (F.E.T.) low noise amplifier having a 40 db gain. An F.E.T. is preferred because of its high input impedance and low noise characteristics. The filters 23 are frequency filters passing only those frequencies relevant for analysis. Filters 23 may be four-pole butterworth active, unity gain filters. A low pass and high pass filter may be cascaded to provide a band-pass filter with adjustable lower and upper limits, having a roll-off of 80 db-decade at both lower and upper cut-offs. The preferred transmitted frequency range is 100 KHz–250 KHz, when detector 14 is a transducer, and 1000 Hz–20 KHz, when detector 14 is an accelerometer.

Logarithmic amplifier 24 enables the monitoring apparatus to analyze very weak as well as very strong signals from the transducer. The logarithmic amplifier may be such that signals ranging from about 300 microvolts to 3 volts are transformed into signals ranging from about 0 volts to 0.5 volts. The secondary amplifier 25 may be a low noise operational amplifier having a 20 db gain stage to amplify the signal to an acceptable level for input into the measuring circuit 18.

Comparator circuit 21 may comprise comparator 26 having two inputs, one connected to the output of logarithmic amplifier 24 and the second connected to a voltage threshold means 34, which may be a variable resistor. The value of threshold means 34 is adjusted, preferably by a control signal from microprocessor 19, to be just above the noise level of the logarithmic amplifier 24. Comparator 26 is turned on when the input signal from logarithmic amplifier 24 rises above this threshold. The comparator 26 in turn switches off when the input voltage falls below this threshold. This action results in a pulse train suitable for input into measuring circuits 16 and 17.

Measuring circuits 16–18 each receive a derivative signal from signal conditioner 15, and each provides a digital output signal representing an emission parameter, such signal being correlatable with the output signal of detector 14, and ultimately, to the acoustic emissions generated in the material. Measuring circuits 16 and 17 receive their input signals from comparator 26, while measuring circuit 18 receives its input signal from secondary amplifier 25.

Measuring circuit 16 may be a total count counter circuit, which accumulates the total number of pulses received from comparator 26 over an interval of time of up to 24 hours. This total time interval may be adjusted by means of a control signal from microprocessor 19. The total count counter circuit may comprise an 8 digit decade counter. When the eighth counter overflows, a service routine of microprocessor 19 may be called which can account for up to 99 overflows, the result being a 10 digit decade counter.

Measuring circuit 17 may be a count rate counter which determines the rate at which total count counter circuit 16 receives the counts. The timing interval of the count rate counter may range from 1 second to 1 hour. The count rate counter may be a 4 digit decade counter. When the fourth decade overflows, it may call for a service routine of microprocessor 19 which can account for up to 99 overflows. The result is a 6 digit counter. The count rate counter output is stored in microprocessor 19 and then the counter is reset.

The output of measuring circuits 16 and 17 is received by microprocessor 19, which in turn subjects such output to an automatic threshold adjustment subroutine, to either accept the output as an acoustic emission signal, or reject the output as background noise. The subroutine samples a number of previously received data points, determines an average value for such points, and automatically adjusts the threshold upwardly or downwardly in accordance therewith. Only output signals having a value greater than the current value of the background noise threshold are considered and stored by microprocessor 19 as being acoustic emission counts.

Measuring circuit 18 may comprise r.m.s. detector 27 and analogue-to-digital (A to D) converter 28. Detector 27 provides a d.c. output equal to the true r.m.s. level of the input signal. The output of detector 27 is fed into A to D converter 28 which may be an 8 bit analogue-to-digital converter where the binary number 00000000 represents 0 and the binary number 11111111 represents 5.12 volts, each binary increase representing an increment of 20 mv. This output is then fed into microprocessor 19, which divides such input by the net amplifier gain to give the true r.m.s. value of the acoustic emission signal. Microprocessor 19 provides control signals to A to D converter 28 in order to control the sampling rate of A to D converter 28 and to synchronize A to D converter 28 with microprocessor 19.

It is to be realized that various other measuring circuits than those described above may be used to analyze acoustic emissions, by obtaining emission signal parameters such as energy event duration, amplitude distribution and frequency content. However, it has been found that the particular selection of parameters generated by the preferred embodiment of this invention provides an excellent basis for accurately detecting and identifying a wide range of problem situations for many applications. It should also be clear that signal conditioner 15 is not limited to the specific circuitry described.

Microprocessor 19 comprises central processing unit (CPU) 29, storage means 30, data input means 31, real time clock 32, communications interface 33 and associated operating system software, master program, and inputted base values of parameters and other data. The central processing unit 29 may be a Z-80 microprocessor based board of 8 bit capacity capable of addressing 64K of random access memory (RAM) and read only memory (ROM). The CPU board may operate on a S-100 bus system. The storage means 30 may comprise RAM and ROM. The ROM may be a 2708 EPROM (Erasable Programmable Read Only Memory). The RAM may be a 32K-byte board, although only one or two K-bytes of RAM is necessary as data storage if the master program resides in ROM. In RAM, there may exist a scratch pad consisting of 15 lines of 16 bytes each.

Real time clock 32 is generated by dividing down the two MHz clock of CPU 29 by two million so as to obtain a 1 Hz square wave. This wave triggers a non-maskable interrupt which in turn calls a clock subroutine of the master program, which updates the hours, minutes and seconds once every second. Simultaneously, two other subroutines of the master program are called, which increment the timing intervals for the count rate counter and the total count counter.

Detector-analyzer units 10 are relatively compact. Their spacing depends upon the attenuation properties and the geometry of the structure being monitored. In the case of a pipeline, it may be possible to space each detector-analyzer unit several hundred meters or more apart, depending upon the sensitivity of the detector. The units may be placed in critical areas of the structure if desired.

Communications means 12 may be a two-way communications link consisting of two UAR-T (Universal Asynchronous Receiver-Transmitter) chips. The transmission medium may be a hard wired configuration, having 9600 bps baud rate in both receive and transmit modes. Alternatively, communications means 12 may comprise radio frequency or microwave broadcasting means, or telephone lines and associated interfaces.

Central control unit 11 may comprise a central processing unit, an input-output unit, a storage medium, and associated operating system software and applications software. Control unit 11 includes means for receiving warning signals from the detector-analyzer units 10, which may be a warning light or audible alarm activated by the warning signal. The control unit 11 may be a 64K-byte, Z-80 based microcomputer operating at 4 MHz equipped with two Shugart disc drives, one for program storage and one for data storage. Central control unit 11 may also comprise a printer and video terminal. Messages received from the detector-analyzer unit 10 may be stored on the data storage disc, or displayed on the video terminal, or printed on paper. The input-output unit, which may comprise a keyboard, is also used to program and communicate with the detector-analyzer units 10, via communications link 12.

In a preferred mode of operation, the central control unit 11, upon power up, addresses each detector-analyzer unit 10 sequentially. As each detector-analyzer unit is addressed, a request is made that it be programmed with its master program. This program includes the emission parameter and base value comparison subroutine, warning signal and message generating subroutines, problem situation characterization subroutine, threshold adjustment subroutine, real time clock subroutine, timer interval subroutines, and other control function subroutines. Sample listings of four of the subroutines of the master program are found in Appendix A. It is to be understood, however, that many variations of these subroutines may be made without departing from the scope of this invention.

Once the master program is transmitted to the detector-analyzer unit, the unit transmits a message to the control unit 11 requesting that 7 variables be entered as follows:
1. time,
2. date,
3. count rate interval,
4. total count interval,
5. r.m.s. base value,
6. count rate base value,
7. total count base value.

Items 3 and 4 represent measurement variables and items 5-7 represent the base values of the emission parameters. This same exercise is carried out in respect of all detector-analyzer units, at which time the system is capable of performing its monitoring tasks.

The monitoring operations of each detector-analyzer unit may be described as follows. As each current parameter value is determined at the end of its respective timing interval (the r.m.s. detector also having a timing interval), it is compared with its respective base value. If the current value of the parameter is less than its respective base value, then the time, date, timing interval and current value of the parameter are memorized on line 1 in the appropriate section of the scratch pad. If the next determined current value is still less than the base value, the new time, date, timing interval and current value are rewritten on line 1. This process continues as long as the current value is less than the respective base value. However, if it is determined that the current value is equal to or greater than the base value, then the above data (time, date, timing interval and current value) is written first on line 1, then sequentially on lines 2 through 5. If the current parameter value should be determined to be less than its base value before line 5 is written, the entire data block is reset and the current data rewritten on line 1. Otherwise, as soon as line 5 is completed, the microprocessor recognizes a problem situation, the problem situation is characterized, and a warning signal is generated. A message containing a characterization of the problem situation, the surveillance unit number, the base value, and the pertinent data block consisting of the time, date, timing interval and current value, are transferred to an output buffer, for communication to the central control unit.

The requirement for 5 consecutive determinations that the current value exceeds the base value is made to reduce the probability of mis-identifying background noise as a problem situation. However, the number of consecutive occurrences required for identification of a problem situation can be reduced or otherwise changed. It can also be set independently for each emission parameter.

The base values of the parameters may be obtained by calibrating a given system against background noise occurring during normal operating conditions.

Each detector-analyzer unit 10 may also include self-diagnostic means for periodically testing the response of the unit. The self-diagnostic means includes pulse generator 20, which is activated by a control signal from real time clock 32, to inject a test pulse of known characteristics into preamplifier 22 or filters 23. The parameters generated by measuring circuit 16, 17 and 18 are then compared by microprocessor 19 to a set of known test pulse parameters stored in storage means 30 of microprocessor 19. A malfunction warning is transmitted by communications means 12 to the central control unit 11 if such comparison reveals a malfunction of the particular detector-analyzer unit. Real time clock 32 may be programmed by a self-diagnostic subroutine to activate pulse generator 20 at regular intervals. The lengths of the intervals may be set for each detector-analyzer unit 10 by central control unit 11.

Central control unit 11 preferably includes means for periodically receiving and storing the current data block (time, date, timing interval and current value of parameter) for one or more emission parameters from a particular detector-analyzer unit. This facility allows for feedback regarding background emissions occurring under normal operating conditions. Such means comprises a subroutine which, in response to a suitable command from the control unit, causes the current data block as described above to be transmitted to the central control unit 11 via communications link 12.

In an alternative embodiment of the invention, there is provided signal processing means coupled to the detector, comprising an analogue-to-digital converter which provides a digitized output signal representative of the output signal of the detector. This signal is directed into the microprocessor, without first generating any emission parameters therefrom. Preferably, measuring circuits 16, 17 and 18 are replaced by a high speed analogue-to-digital (A to D) converter. The output of the A to D converter is then fed directly into data input means 31 of microprocessor 19. The data signal received by microprocessor 19 is therefore representative of the high frequency acoustic emission wave packet itself.

A set of emission parameters analogous to those generated by the measuring circuits may be generated by microprocessor 19 itself, by means of suitable applications software, capable of transforming the stored data signals into emission parameters such as total counts, count rate and r.m.s. voltage, by means of appropriate algorithms. The current values of the emission parameters may then be compared, in a manner similar to that of the preferred embodiment, with the base values for these parameters (which are stored in memory), to generate a warning signal, if any of the current values exceed their respective base values.

It will be recognized that this alternative embodiment may not possess all of the advantages of the preferred embodiment of the invention, since the alternative embodiment does not address the problems associated with the digitization of high frequency data and the need for a microprocessor having an extremely large data storage capacity. The preferred embodiment may also be advantageous over the alternative embodiment since the preferred embodiment may not require as much time to process a particular acoustic emission event. In the alternative embodiment, due to data storage limitations, the data representing a particular acoustic emission event usually has to be fully processed and analyzed before a signal representing another acoustic emission event can be stored. Accordingly, such a system is usually only capable of receiving data during a fraction of the time that the system is on-line, due to limitations of currently available microprocessors.

While the present invention has been described and illustrated with respect to the preferred embodiment, those skilled in the art will understand that numerous variations of the preferred embodiment may be made without departing from the scope of the invention, which is defined in the appended claims.

APPENDIX A

**\*\*BALANCE OF NON-MASK INT. SERVICE SUBROUTINE\*\***

PURPOSE: Used to call the subroutines used in arithmetic and logical processing of obtained data.

```
1634   CDE910    CALL   10E9
1637   CD5813    CALL   1358
163A   F5        PUSH   AF
163B   3A2738    LD     A,(3827)
163E   FE00      CP     00
1640   2005      JR     NZ,05
1642   CD9816    CALL   1698
1645   1821      JR     21
1647   FE01      CP     01
1649   2008      JR     NZ,08
164B   CD9816    CALL   1698
164E   CD2217    CALL   1722
1651   1815      JR     15
1653   FE02      CP     02
1655   2008      JR     NZ,08
1657   CD9816    CALL   1698
165A   CDA917    CALL   17A9
165D   1809      JR     09
165F   CD9816    CALL   1698
```

```
1662  CD2217  CALL  1722
1665  CDA917  CALL  17A9
1668  3A1A38  LD    A,(381A)
166B  FE05    CP    05
166D  2005    JR    NZ,05
166F  CD0A19  CALL  190A
1672  1816    JR    16
1674  3A1B38  LD    A,(381B)
1677  FE05    CP    05
1679  2005    JR    NZ,05
167B  CDDC19  CALL  19DC
167E  180A    JR    0A
1680  3A1C38  LD    A,(381C)
1683  FE05    CP    05
1685  2003    JR    NZ,03
1687  CDAE1A  CALL  1AAE
168A  CDFC11  CALL  11FC
168D  CD4412  CALL  1244
1690  CDBA12  CALL  12BA
1693  CD9716  CALL  1697
1696  F1      POP   AF
1697  C9      RET
*
```

**\*\*SUBROUTINE\*\***

PURPOSE: Used to determine whether current parameter(acoustic) is less than or greater then the corresponding base value. This routine also channels all output data in one of five running lines. (r.m.s. data only).

```
1698  C5      PUSH  BC
1699  D5      PUSH  DE
169A  E5      PUSH  HL
169B  F5      PUSH  AF
169C  0602    LD    B,02
169E  111138  LD    DE,3811
16A1  211E38  LD    HL,381E
16A4  A7      AND   A
16A5  1A      LD    A,(DE)
16A6  9E      SBC   A,(HL)
16A7  27      DAA
16A8  1B      DEC   DE
16A9  2B      DEC   HL
16AA  10F9    DJNZ,F9
16AC  3037    JR    NC,37
16AE  211A38  LD    HL,381A
16B1  7E      LD    A,(HL)
16B2  FE00    CP    00
16B4  280F    JR    Z,0F
16B6  3600    LD    (HL),00
16B8  214F39  LD    HL,394F
16BB  3600    LD    (HL),00
16BD  114E39  LD    DE,394E
16C0  014F00  LD    BC,004F
16C3  EDB8    LDDR
16C5  110039  LD    DE,3900
16C8  210038  LD    HL,3800
16CB  010600  LD    BC,0006
16CE  EDB0    LDIR
16D0  EB      EX    DE,HL
16D1  3600    LD    (HL),00
```

```
16D3   23       INC   HL
16D4   3600     LD    (HL),00
16D6   23       INC   HL
16D7   3601     LD    (HL),01
16D9   23       INC   HL
16DA   EB       EX    DE,HL
16DB   211038   LD    HL,3810
16DE   010200   LD    BC,0002
16E1   EDBC     LDIR
16E3   1838     JR    38
16E5   211A38   LD    HL,381A
16E8   7E       LD    A,(HL)
16E9   FE00     CP    00
16EB   2003     JR    NZ,03
16ED   34       INC   (HL)
16EE   18D5     JR    D5
16E0   EE01     CP    01
16F2   2006     JR    NZ,06
16F4   34       INC   (HL)
16F5   111039   LD    DE,3910
16F8   18CE     JR    CE
16FA   FE02     CP    02
16FC   2006     JR    NZ,06
16FE   34       INC   (HL)
16FF   112039   LD    DE,3920
1702   18C4     JR    C4
1704   FE03     CP    03
1706   2006     JR    NZ,06
1708   34       INC   (HL)
1709   113039   LD    DE,3930
170C   18BA     JR    BA
170E   FE04     CP    04
1710   2006     JR    NZ,06
1712   34       INC   (HL)
1713   114039   LD    DE,3940
1716   18B0     JR    B0
1718   3600     LD    (HL),00
171A   34       INC   (HL)
171B   189B     JR    9B
171D   F1       POP   AF
171E   E1       POP   HL
171F   D1       POP   DE
1720   C1       POP   BC
1721   C9       RET
*
```

SUBROUTINE

PURPOSE: Used to determine whether current parameter(acoustic) is , < or ≥ then its corresponding base value. This routine also channels all data in one of five lines.
(count rate data only).

```
1722   C5       PUSH  BC
1723   D5       PUSH  DE
1724   E5       PUSH  HL
1725   F5       PUSH  AF
1726   0603     LD    B,03
1728   111438   LD    DE,3814
172B   212C38   LD    HL,382C
172E   A7       AND   A
172F   1A       LD    A,(DE)
```

```
1730   9E       SBC   A,(HL)
1731   27       DAA
1732   1B       DEC   DE
1733   2B       DEC   HL
1734   10F9     DJNZ  F9
1736   3034     JR    NC,34
1738   211B38   LD    HL,381B
173B   7E       LD    A,(HL)
173C   FE00     CP    00
173E   280F     JR    Z,0F
1740   3600     LD    (HL),00
1742   219F39   LD    HL,399F
1745   3600     LD    (HL),00
1747   119E39   LD    DE,399E
174A   014F00   LD    BC,004F
174D   EDB8     LDDR
174F   115039   LD    DE,3950
1752   210038   LD    HL,3800
1755   010600   LD    BC,0006
1758   EDB0     LDIR
175A   21A012   LD    HL,12A0
175D   010300   LD    BC,0003
1760   EDB0     LDIR
1762   211238   LD    HL,3812
1765   010300   LD    BC,0003
1768   EDB0     LDIR
176A   1838     JR    38
176C   211B38   LD    HL,381B
176F   7E       LD    A,(HL)
1770   FE00     CP    00
1772   2003     JR    NZ,03
1774   34       INC   (HL)
1775   18D8     JR    D8
1777   FE01     CP    01
1779   2006     JR    NZ,06
177B   34       INC   (HL)
177C   116039   LD    DE,3960
177F   18D1     JR    D1
1781   FE02     CP    02
1783   2006     JR    NZ,06
1785   34       INC   (HL)
1786   117039   LD    DE,3970
1789   18C7     JR    C7
178B   FE03     CP    03
178D   2006     JR    NZ,06
178F   34       INC   (HL)
1790   118039   LD    DE,3980
1793   18BD     JR    BD
1795   FE04     CP    04
1797   2006     JR    NZ,06
1799   34       INC   (HL)
179A   119039   LD    DE,3990
179D   18B3     JR    B3
179F   3600     LD    (HL),00
17A1   34       INC   (HL)
17A2   189E     JR    9E
17A4   F1       POP   AF
17A5   E1       POP   HL
17A6   D1       POP   DE
17A7   C1       POP   BC
17A8   C9       RET
*
```

SUBROUTINE

PURPOSE: Used to determine whether current parameter(acoustic) is
, < or ≥ then its corresponding base value. This routine also
channels all output data in one of five running lines.
(total count data only).

```
17A9   C5          PUSH    BC
17AA   D5          PUSH    DE
17AB   E5          PUSH    HL
17AC   F5          PUSH    AF
17AD   0605        LD      B,05
17AF   111938      LD      DE,3819
17B2   213438      LD      HL,3834
17B5   A7          AND     A
17B6   1A          LD      A,(DE)
17B7   9E          SBC     A,(HL)
17B8   27          DAA
17B9   1B          DEC     DE
17BA   2B          DEC     HL
17BB   10F9        DJNZ,F9
17BD   3034        JR      NC,34
17BF   211C38      LD      HL,381C
17C2   7E          LD      A,(HL)
17C3   FE00        CP      00
17C5   280F        JR      Z,0F
17C7   3600        LD      (HL),00
17C9   21EF39      LD      HL,39EF
17CC   3600        LD      (HL),00
17CE   11EE39      LD      DE,39EE
17D1   014F00      LD      BC,004F
17D4   EDB8        LDDR
17D6   11A039      LD      DE,39A0
17D9   210038      LD      HL,3800
17DC   010600      LD      BC,0006
17DF   EDB0        LDIR
17E1   21B712      LD      HL,12B7
17E4   010300      LD      BC,0003
17E7   EDB0        LDIR
17E9   211538      LD      HL,3815
17EC   010500      LD      BC,0005
17EF   EDB0        LDIR
17F1   1838        JR      38
17F3   211C38      LD      HL,381C
17F6   7E          LD      A,(HL)
17F7   FE00        CP      00
17F9   2003        JR      NZ,03
17FB   34          INC     (HL)
17FC   18D8        JR      D8
17FE   FE01        CP      01
1800   2006        JR      NZ,06
1802   34          INC     (HL)
1803   11B039      LD      DE,39B0
1806   18D1        JR      D1
1808   FE02        CP      02
180A   2006        JR      NZ,06
180C   34          INC     (HL)
180D   11C039      LD      DE,39C0
1810   18C7        JR      C7
1812   FE03        CP      03
1814   2006        JR      NZ,06
1816   34          INC     (HL)
```

```
1817   11D039   LD    DE,39D0
181A   18BD     JR    BD
181C   FE04     CP    04
181E   2006     JR    NZ,06
1820   34       INC   (HL)
1821   11E039   LD    DE,39E0
1824   18B3     JR    B3
1826   3600     LD    (HL),00
1828   34       INC   (HL)
1829   189E     JR    9E
182B   F1       POP   AF
182C   E1       POP   HL
182D   D1       POP   DE
182E   C1       POP   BC
182F   C9       RET
*
```

We claim:

1. Apparatus suitable for continuous long-term monitoring of acoustic emissions, comprising:
   (a) a plurality of detector-analyzer units, each for placement in a discrete pre-selected location, each detector-analyzer unit including:
      (i) an acoustic detector for detecting acoustic emission and providing an output signal representative of the acoustic emission;
      (ii) signal processing means coupled to the detector and receiving the output signal thereof and providing at least one derivative output signal having characteristics correlatable with preselected characteristics of the output signal of the detector; and
      (iii) a microprocessor coupled to the signal processing means for receiving the at least one derivative output signal thereof, including means for determining a current value of each of a set of emission parameters from the at least one derivative output signal, means for storing a set of base values for each of the set of emission parameters, means for periodically comparing the current value of each of the set of emission parameters with the base value thereof to determine the existence of a problem situation, and means for providing a warning signal if the current value of any of the set of emission parameters exceeds the base value thereof; and
   (b) a central control unit remote from and coupled by communication means to each of said detector-analyzer units, for receiving any warning signals generated by any of the detector-analyzer units.

2. Apparatus as defined in claim 1, wherein the microprocessor of each detector-analyzer unit also includes means for controlling the operation of the signal processing means.

3. Apparatus as defined in claim 1, wherein the control unit further comprises means for periodically receiving from each detector-analyzer unit and storing for use the current values of one or more of the set of emission parameters in order to monitor the background acoustic emissions when a problem situation is not occurring.

4. Apparatus as defined in claim 1, wherein the microprocessor of each detector-analyzer unit also includes means for providing a message when a problem situation is determined, said message including a signal identifying the respective detector-analyzer unit which generated the warning signal, and the central control unit includes means for receiving such message via the communications means.

5. Apparatus as defined in claim 4, wherein said message additionally includes a signal representing current values of the emission parameters at the time the warning signal was generated.

6. Apparatus as defined in claim 1, wherein the microprocessor of each detector-analyzer unit includes means for characterizing particular problem situations, comprising means for storing a set of problem situation identifiers correlatable with a determination that one or more emission parameters have exceeded their base values, means for making such a determination, and means for providing a signal receivable by the central control unit via the communications means representing the appropriate problem situation identifiers.

7. Apparatus as defined in claim 1, wherein the communications means is a two-way communications link.

8. Apparatus as defined in claim 7, wherein the central control unit includes means for programming the detector-analyzer units with a given set of base values via the communications link.

9. Apparatus as defined in claim 8, wherein the central control unit includes means for independently programming each unit with a discrete set of base values.

10. Apparatus as defined in claim 7, wherein the central control unit includes means for programming and re-programming each detector-analyzer unit with its master program by means of the communications link.

11. Apparatus as defined in claim 1, wherein the microprocessor of each detector-analyzer unit provides a warning signal if one or more members of the set of emission parameters exceed the respective base values thereof.

12. Apparatus as defined in claim 1, wherein the acoustic detector is a piezoelectric transducer.

13. Apparatus as defined in claim 1, wherein the acoustic detector is an accelerometer.

14. Apparatus as defined in claim 1, wherein each of the detector-analyzer units further comprises self-diagnostic means for injecting a test pulse at pre-selected intervals into the signal conditioner, for comparing the response thereto with a known response, and for transmitting a warning signal to the central control unit if the comparison reveals a malfunction of the detector-analyzer unit.

15. Apparatus as defined in claim 1, wherein the signal processing means comprises:
   (i) at least one signal conditioner coupled to the detector for receiving the output signal thereof and providing at least one derivative signal having characteristics correlatable with preselected characteristics of the output signal of the detector; and (ii) at least one measuring circuit coupled to the signal conditioner for receiving each such derivative signal, and providing for each such derivative signal a digital output signal representing one of a set of emission parameters, correlatable with said preselected characteristics of the output signal of the detector.

16. Apparatus as defined in claim 15, wherein the microprocessor includes threshold adjustment means for characterizing the output signal from the at least one measuring circuit as being either an acoustic emission signal or background noise, based upon whether the output signal exceeds an average noise value determined from a sampling or earlier received output signals from the at least one measuring circuit.

17. Apparatus as defined in claim 15, wherein the at least one signal conditioner comprises at least one frequency filter and at least one signal amplifier.

18. Apparatus as defined in claim 15, wherein one of the signal conditioners comprises a comparator circuit for generating a pulse train suitable for input into at least one of the measuring units.

19. Apparatus as defined in claim 15, wherein the at least one measuring circuit comprises a total count counter circuit, and wherein the set of emission parameters comprises total counts, count rate and r.m.s. voltage.

20. Apparatus as defined in claim 19, wherein the microprocessor includes real time clock means for controlling the operation of the total count counter circuit, count rate counter circuit, and r.m.s. volt meter circuit.

21. Apparatus as defined in claim 19, wherein one of the signal conditioners comprises a comparator circuit for generating a pulse train suitable for input into the count rate counter circuit and the total count counter circuit, respectively.

22. A detector-analyzer unit, for use with a remote central control unit, the combination thereof being suitable for continuous monitoring of acoustic emissions, the said detector-analyzer unit comprising:
 (i) an acoustic detector for detecting acoustic emission and providing an output signal representative of the acoustic emission;
 (ii) at least one signal conditioner coupled to the detector and receiving the output signal thereof and providing at least one derivative signal having characteristics correlatable with preselected characteristics of the output signal of the detector;
 (iii) at least one measuring circuit coupled to the signal conditioner and receiving each such derivative signal, and providing for each such derivative signal a digital output signal representing one of a set of emission parameters, correlatable with said pre-selected characteristics of the output signal of the detector; and
 (iv) a microprocessor coupled to each such measuring circuit and storing a set of base values and receiving and storing a digital output signal representing the set of emission parameters, said microprocessor periodically comparing members of the set of base values with corresponding members of the set of emission parameters to determine the existence of a problem situation, and providing a warning signal if any such problem situation is perceived.

23. The detector-analyzer unit as defined in claim 22, wherein the microprocessor further comprises means for controlling the function of the at least one measuring circuit.

24. The detector-analyzer unit as defined in claim 22, wherein the microprocessor further comprises means for providing a message in addition to the warning signal when a problem situation is perceived, said message including a signal identifying the said microprocessor.

25. The detector-analyzer unit as defined in claim 22, wherein the microprocessor provides a warning signal if one or more members of the set of emission parameters exceed the respective base values thereof.

26. The detector-analyzer unit as defined in claim 22, wherein the microprocessor includes means for characterizing particular problem situations, comprising means for storing a set of problem situation identifiers correlatable with a determination that one or more emission parameters have exceeded their base values, means for making such a determination, and means for providing a signal receivable by the central control unit via the communication means representing the appropriate problem situation identifiers.

27. The detector-analyzer unit as defined in claim 22, further comprising self-diagnostic means for injecting a test pulse at pre-selected intervals into the signal conditioner, for comparing the response thereto with a known response, and for transmitting a warning signal to the remote central control unit if the comparison reveals a malfunction of the detector-analyzer unit.

28. The detector-analyzer unit as defined in claim 22, wherein one of the signal conditioners comprises a comparator circuit for generating a pulse train suitable for input into at least one of the measuring circuits.

29. The detector-analyzer unit as defined in claim 22, wherein the microprocessor includes threshold adjustment means for characterizing the output signal from the at least one measuring circuit as being either an acoustic emission signal or background noise, based upon whether the output signal exceeds an average noise value determined from a sampling of earlier received output signals from the at least one measuring circuit.

30. The detector-analyzer unit as defined in claim 22, wherein the at least one measuring circuit comprises a total count counter circuit, a count rate counter circuit, and an r.m.s. voltmeter circuit, and wherein the set of emission parameters comprises total counts, count rate and r.m.s. voltage.

31. The detector-analyzer unit as defined in claim 30, wherein the microprocessor includes real time clock means for controlling the operation of the total count counter circuit, count rate counter circuit, and r.m.s. volt meter circuit.

32. Apparatus suitable for continuous long-term monitoring of acoustic emissions, comprising:
 (a) a plurality of detector-analyzer units, each for placement in a discrete pre-selected location, each detector-analyzer unit including:
  (i) an acoustic detector for detecting acoustic emission and providing an output signal representative of the acoustic emission;
  (ii) at least one signal conditioner coupled to the detector and receiving the output signal thereof and providing at least one derivative signal having characteristics correlatable with preselected characteristics of the output signal of the detector;

(iii) at least one digitizing circuit coupled to the signal conditioner and receiving each such derivative signal, and providing for each such derivative signal a digital output signal correlatable with said pre-selected characteristics of the output signal of the detector; and (iv) a microprocessor coupled to each such digitizing circuit and receiving the output signal thereof, including means for periodically determining a current value of each of a set of emission parameters from the digital output signal, means for storing a set of base values for each of the set of emission parameters, means for periodically comparing the current value of each of the set of emission parameters with the base value thereof to determine the existence of a problem situation, and means for providing a warning signal if the current value of any of the set of emission parameter exceeds the base value thereof; and (b) a central control unit remote from and coupled to each of said detector-analyzer units, for receiving any warning signals generated by any of the detector-analyzer units.

33. A detector-analyzer unit, for use with a remote central control unit, the combination thereof being suitable for continuous monitoring of acoustic emissions, the said detector-analyzer unit comprising:

(i) an acoustic detector for detecting acoustic emission and providing an output signal representative of the acoustic emission;

(ii) signal processing means coupled to the detector and receiving the output signal thereof and providing at least one derivative digitized output signal having characteristics correlatable with preselected characteristics of the output signal of the detector; and (iii) a microprocessor coupled to the signal processing means and receiving the output signal thereof, including means for determining a current value of each of a set of emission parameters from the digital output signal, means for storing a set of base values for each of the set of emission parameters, means for periodically comparing the current value of each of the set of emission parameters with the base value thereof to determine the existence of a problem situation, and means for providing a warning signal if the current value of any of the set of emission parameter exceeds the base value thereof.

* * * * *